US011149188B2

(12) United States Patent
Recio, III et al.

(10) Patent No.: US 11,149,188 B2
(45) Date of Patent: Oct. 19, 2021

(54) OLEOFURANSULFONATE SURFACTANTS FOR USE IN WELLBORE APPLICATIONS

(71) Applicant: Halliburton Energy Services, Inc., Houston, TX (US)

(72) Inventors: Antonio Recio, III, Humble, TX (US); Janette Cortez, Porter, TX (US); Hong Sun, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 16/820,277

(22) Filed: Mar. 16, 2020

(65) Prior Publication Data

US 2020/0308475 A1 Oct. 1, 2020

Related U.S. Application Data

(60) Provisional application No. 62/825,533, filed on Mar. 28, 2019.

(51) Int. Cl.

| | |
|---|---|
| ***C09K 8/035*** | (2006.01) |
| ***C09K 8/60*** | (2006.01) |
| ***C09K 8/03*** | (2006.01) |
| *C01B 33/12* | (2006.01) |
| *C08L 33/26* | (2006.01) |
| *C07D 307/64* | (2006.01) |

(52) U.S. Cl.

CPC .............. *C09K 8/602* (2013.01); *C09K 8/032* (2013.01); *C09K 8/035* (2013.01); *C01B 33/12* (2013.01); *C07D 307/64* (2013.01); *C08L 33/26* (2013.01); *C09K 2208/10* (2013.01)

(58) Field of Classification Search

CPC ....... C01B 33/12; C07D 307/64; C08L 33/26; C09K 2208/10; C09K 2208/28; C09K 8/032; C09K 8/035; C09K 8/12; C09K 8/42; C09K 8/584; C09K 8/588; C09K 8/602; C09K 8/68; C09K 8/74; C09K 8/882

See application file for complete search history.

(56) References Cited

U.S. PATENT DOCUMENTS 5,960,880 A * 10/1999 Nguyen ............... C09K 8/5755 166/280.1

2015/0152329 A1* 6/2015 Seetharaman ....... C07D 257/04 422/16

(Continued)

OTHER PUBLICATIONS

D.S. Park, et al.; "Tunable Oleo-Furan Surfactants by Acylation of Renewable Furans"; ACS Central Science—Research Article; Oct. 29, 2016, 2, p. 820-824.

(Continued)

*Primary Examiner* — Alicia Bland

(74) *Attorney, Agent, or Firm* — McGuireWoods LLP

(57) ABSTRACT

Treatment fluids and associated methods for treating a subterranean formation. An example method includes introducing a treatment fluid into a wellbore penetrating the subterranean formation. The treatment fluid includes an oleofuransulfonate surfactant; a treatment fluid additive capable of interaction with a cation; and an aqueous fluid. The cation is present in the treatment fluid or contacts the treatment fluid. The method further includes solvating the treatment fluid additive with the oleofuransulfonate surfactant.

9 Claims, 2 Drawing Sheets

(56) References Cited

U.S. PATENT DOCUMENTS

| | | | | |
|---|---|---|---|---|
| 2016/0264836 | A1* | 9/2016 | Wang | C09K 8/20 |
| 2018/0327375 | A1* | 11/2018 | Krumm | C07D 307/64 |
| 2018/0327376 | A1* | 11/2018 | Park | C07D 307/36 |

OTHER PUBLICATIONS

K. E. Joseph; "Tunable Synthesis and Characterization of Oleo-Furan Sulfonate Surfactants from Renewable Furan and Fatty Acids"; Dissertation submitted to the faculty of University of Minnesota; May 2018.

* cited by examiner

OLEOFURANSULFONATE SURFACTANTS FOR USE IN WELLBORE APPLICATIONS

TECHNICAL FIELD

The present disclosure relates generally to wellbore operations, and more particularly, to wellbore operations utilizing oleofuransulfonate surfactants to, amongst other reasons, reduce the impact of dissolved cations on treatment fluid additives in hard brines.

BACKGROUND

Hydrocarbon producing formations may be stimulated by hydraulic fracturing treatments. In traditional hydraulic fracturing operations, a fracturing fluid (e.g., pad fluid, proppant-laden fluid, etc.) is pumped at a rate and pressure sufficient to create or enhance one or more fractures in the formation. Some fracturing fluids have low viscosities. These types of fracturing fluids are sometimes referred to as slickwater fluids. Due to their low viscosity, proppant transport may be achieved by increasing pumping rates. However, this may result in energy loss due to friction between the tubulars and the turbulent fluid flow. A friction reducer may be used to reduce the horsepower requirement during the fracturing treatment by changing the turbulent flow to a laminar flow in the tubulars.

Reducing the friction of the fracturing fluid may be beneficial for forming complex fracture networks in some formations, for example, tight shale formations. However, in order to function as desired, the friction reducer polymers should not interact with cations (e.g., Na, K, Ca, Mg, Ba, Fe, etc.) present in the treatment fluid, the formation, or produced from wellbore operations such as acidizing. In particular, hard brines (e.g., produced waters) have a high salinity that can affect their performance in some wellbore operations and may require the use of complex mixtures of chemical additives to reduce the impact of the dissolved solids on other treatment fluid additives such as friction reducing polymers. The present disclosure provides improved methods and compositions for treating formations through the use of oleofuransulfonate surfactants.

BRIEF DESCRIPTION OF THE DRAWINGS

Illustrative examples of the present disclosure are described in detail below with reference to the attached drawing figures, which are incorporated by reference herein, and wherein.

Figure 1:
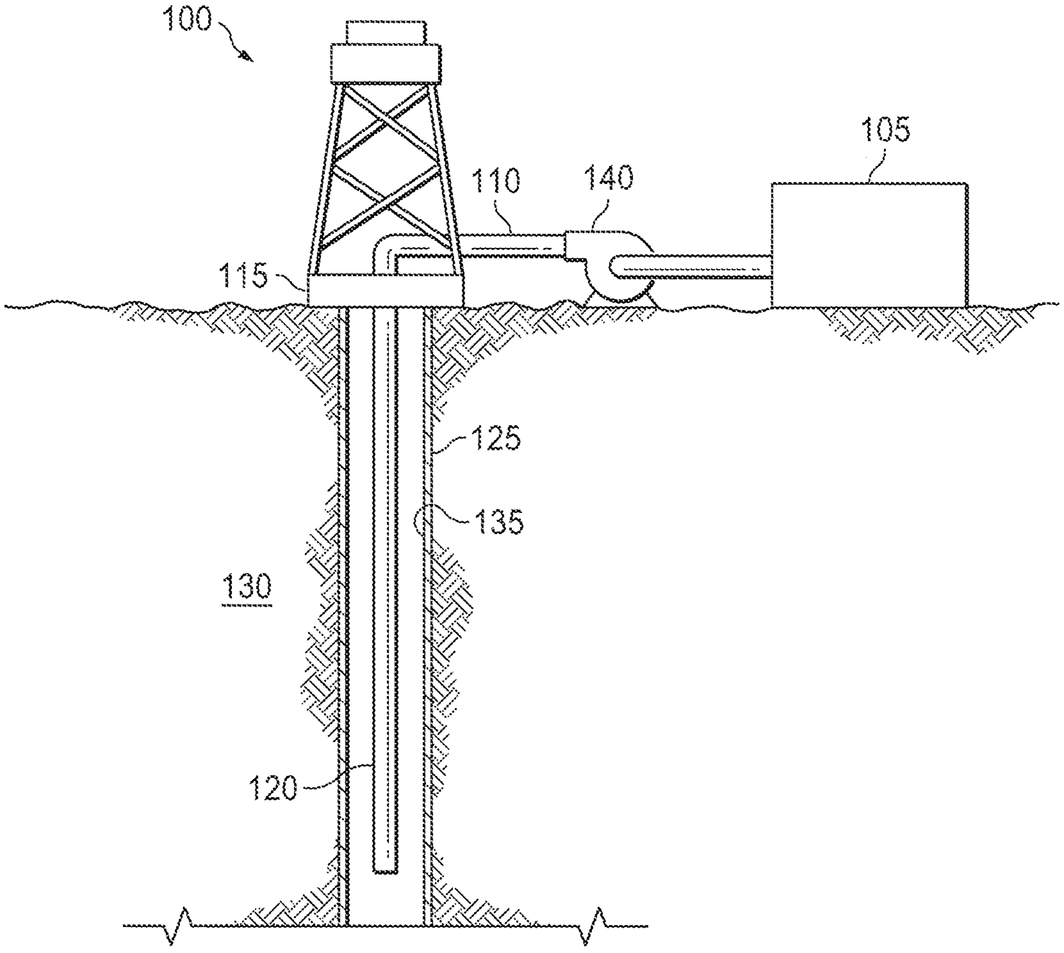
FIG. 1 is a schematic illustrating a system of surface equipment for the preparation and delivery of a treatment fluid to a wellbore in accordance with one or more examples described herein.

The illustrated figures are only exemplary and are not intended to assert or imply any limitation with regard to the environment, architecture, design, or process in which different examples may be implemented.

DETAILED DESCRIPTION

The present disclosure relates generally to wellbore operations, and more particularly, to wellbore operations utilizing oleofuransulfonate surfactants to, amongst other reasons, reduce the impact of dissolved cations on treatment fluid additives in hard brines.

In the following detailed description of several illustrative examples, reference is made to the accompanying drawings that form a part hereof, and in which is shown by way of illustration, examples that may be practiced. These examples are described in sufficient detail to enable those skilled in the art to practice them, and it is to be understood that other examples may be utilized and that logical structural, mechanical, electrical, and chemical changes may be made without departing from the spirit or scope of the disclosed examples. To avoid detail not necessary to enable those skilled in the art to practice the examples described herein, the description may omit certain information known to those skilled in the art. The following detailed description is, therefore, not to be taken in a limiting sense, and the scope of the illustrative examples are defined only by the appended claims.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the examples of the present disclosure. At the very least, and not as an attempt to limit the application of the doctrine of equivalents to the scope of the claim, each numerical parameter should at least be construed in light of the number of reported significant digits and by applying ordinary rounding techniques. It should be noted that when "about" is at the beginning of a numerical list, "about" modifies each number of the numerical list. Further, in some numerical listings of ranges some lower limits listed may be greater than some upper limits listed. One skilled in the art will recognize that the selected subset will require the selection of an upper limit in excess of the selected lower limit.

Unless otherwise specified, any use of any form of the terms "connect," "engage," "couple," "attach," or any other term describing an interaction between elements is not meant to limit the interaction to direct interaction between the elements and may also include indirect interaction between the elements described. Further, any use of any form of the terms "connect," "engage," "couple," "attach," or any other term describing an interaction between elements includes items integrally formed together without the aid of extraneous fasteners or joining devices. In the following discussion and in the claims, the terms "including" and "comprising" are used in an open-ended fashion, and thus should be interpreted to mean "including, but not limited to." Unless otherwise indicated, as used throughout this document, "or" does not require mutual exclusivity.

The terms uphole and downhole may be used to refer to the location of various components relative to the bottom or end of a well. For example, a first component described as uphole from a second component may be further away from the end of the well than the second component. Similarly, a first component described as being downhole from a second component may be located closer to the end of the well than the second component.

As used herein, the term "formation" encompasses the term "reservoir," referring to a portion of the formation which has sufficient porosity and permeability to store or transmit fluids (e.g., hydrocarbons). As used herein, the term "treatment fluid" refers generally to any fluid that may be used in a subterranean application in conjunction with a desired function and/or for a desired purpose. The term "treatment fluid" does not imply any particular action by the fluid or any component thereof.

The examples described herein relate to the use of oleofuransulfonate surfactants (hereafter "OFS surfactants") in wellbore operations. The OFS surfactants may be provided to a treatment fluid intended to be introduced into a wellbore penetrating a subterranean formation. The treatment fluid may comprise a treatment fluid additive, (e.g., a polymeric friction reducer) that is susceptible to interaction with cations (e.g., any mono-, di-, or trivalent cation). Advantageously, the OFS surfactants form stable micelles at or aggregations at low concentrations requiring fewer OFS surfactant molecules to form aggregates or a micelle sufficient for improving the solubility profile of the polymer or solvating a treatment fluid additive in the core of the micelle. A further advantage is that the OFS surfactants form both aggregates and/or micelles that are stable at high concentrations of dissolved cations (e.g., cation concentrations exceeding 100,000 ppm). This increased stability of the micelles may be imparted to treatment fluid additives in the treatment fluid, effectively shielding the treatment fluid additives from cation interactions that could induce undesirable conformation changes in the treatment fluid additives. An additional advantage is that the OFS surfactants may allow for the use of hard brines (e.g., produced waters, TDS>10,000 ppm) as the base fluid in wellbore operations. Another advantage is that the OFS surfactants may reduce the need to use mitigating treatment fluid additives such as chelants or chelating agents (e.g., ethylenediaminetetraacetic acid, ethylenediamine, phosphates, zeolites, citrates, polycarboxylates, sodium tripolyphosphates, etc.), cationic surfactants, dimeric ammonium salts, and the like. As such, the treatment fluids may be free of chelants, cationic surfactants, dimeric ammonium salts, and the like. A further advantage is that the OFS surfactants may be used with any polymeric material that can function as a friction reducer or drag reducer. In some treatment fluid operations, a class of polymers know as partially hydrolyzed polymers (e.g., partially hydrolyzed polyacrylamide friction reducers) may be constructed having some sulfonic and/or hydrophobic monomers incorporated into the backbone to improve salt tolerance. As an example, partially hydrolyzed polyacrylamide friction reducers constructed from [2-(acryloyloxy)ethyl]trimethylammonium chloride monomers and/or 2-acrylamido-2-methylpropane sulfonic acid monomers (or salts thereof) may be used in treatment fluids to improve performance of the partially hydrolyzed polyacrylamide friction reducers in high salt environments or high salt base fluids. These specialized friction reducers may be expensive to produce. As such, the OFS surfactants may reduce costs by allowing the use of any partially-hydrolyzed polymer, including those lacking sulfonic and/or cationic monomers, such as the aforementioned [2-(acryloyloxy)ethyl]trimethylammonium chloride monomers and/or 2-acrylamido-2-methylpropane sulfonic acid monomers. A still further advantage is that the OFS surfactants may not impact the functionality of the treatment fluid.

The treatment fluid comprises an OFS surfactant. Generally, the OFS surfactant may be any oleofuransulfonate suitable for use in the treatment fluids disclosed herein. Generally, the OFS surfactants comprise a sulfonate group bound to a furan linker that is bound to any hydrophobic alkyl chain (e.g., a fatty acid). The sulfonated furan ring forms the hydrophilic polar head group of the surfactant and the carbon chain of the hydrophobic alkyl chain forms the hydrophobic tail of the surfactant. Without limitation, the Stern layer (i.e., polar head aggregates of micelles directly interacting with cations in the bulk aqueous phase) of the micelle may be increased as the polar head group of the OFS surfactant is increased relative to non-OFS surfactants. This increase in the Stern layer may result in the OFS surfactants repelling the cations further from the treatment fluid additive solvated in the micelle core relative to a non-OFS surfactant having a smaller polar head group. As such, the potential opportunities for interaction between the treatment fluid additive and a cation are reduced.

The length of the carbon chain the hydrophobic tail may be adjusted as desired to adjust the properties (e.g., the critical micelle concentration) of the OFS surfactants. The hydrophobic alkyl chain may comprise a side chain to add additional functionality to the OFS surfactants. The hydrophobic alkyl chain may be branched or linear. If the hydrophobic alkyl chain comprises a fatty acid, the side chain may be bound to the acid portion of the fatty acid.

The OFS surfactants may be prepared by any suitable method as would be readily apparent to one of ordinary skill in the art. Generally, the furan may be bound to the hydrophobic alkyl chain using Friedel-Crafts acylation or alkylation. For example, the furan may be reacted with the anhydride form of a fatty acid in the presence of a solid acid (e.g., Lewis acid zeolites or Bronstead acid zeolites) to produce an acylated furan ketone. Alternatively, the fatty acid may be directly acylated and reacted with the furan in the presence of small anhydrides having strong electron withdrawing groups (e.g., trifluroacetic anhydride) to produce the acylated furan ketone. The acylated furan ketone may then be produced into the desired OFS surfactant with a variety of potential reactions that will yield different species of hydrophobic alkyl chains for the tail portion of the OFS surfactant. For example, an aldol condensation, reduction, and then sulfonation of the acylated furan ketone may produce an OF S surfactant with a branched alkyl chain. Reduction and sulfonation of the acylated furan ketone may produce an OFS surfactant with a linear alkyl chain. Direct sulfonation of the acylated furan ketone may produce an OFS surfactant. The acid terminal end of the fatty acid is bound to the furan linker in this species. Control of the final structure of the hydrophobic alkyl chain allows for control over some of the properties of the OFS surfactants, for example, the critical micelle concentration of the OFS surfactants. The OFS surfactants may thus be adapted as desired to provide the greatest efficacy against the cations encountered during treatment. It is to be understood that the OFS surfactants may be prepared in a variety of ways as would be apparent to one of ordinary skill in the art, and this disclosure is not limited to any specific preparation method for the OFS surfactants.

Specific examples of the OFS surfactants include, but are not limited to, 5-(1-oxododecyl)-2-furansulfonic acid; 5-(1-hexatetradecyl)-2-furansulfonic acid; 5-(1-oxohexadecyl)-2-furansulfonic acid; 5-(1-oxooctadecyl)-2-furansulfonic acid; 5-heptyl-2-furansulfonic acid; 5-dodecyl-2-furansulfonic acid; 5-tridecyl-2-furansulfonic acid; 5-tetradecyl-2-furansulfonic acid; 5-octadecyl-2-furansulfonic acid; 5-(2-ethyldodecyl)-2-furansulfonic acid; 5-methyl-2,4-furandisulfonic acid; 5-ethyl-2-pentyl-3-furansulfonic acid; 5-ethyl-2-hexyl-3-furansulfonic acid; 2-ethyl-5-hexyl-3-furansulfonic acid; 5-ethyl-2-(1-hydroxyhexyl)-3-furansulfonic acid; 5-ethyl-2-furansulfonic acid; 5-(1-methylundecyl)-2-furansulfonic acid; 5-(1-methyldecyl)-2-furansulfonic acid; 5-ethyl-2-(1-hydroxyhexyl)-3-furansulfonic acid; 5-ethyl-2-(1-oxohexyl)-3-furansulfonic acid; 5-(2-hydroxyethyl)-2-furansulfonic acid; 5-(2-hydroxyethyl)-2-(1-hydroxyhexyl)-3-furansulfonic acid; any salts thereof; any derivatives thereof; and any combination thereof.

An additional example of an OFS surfactant includes:

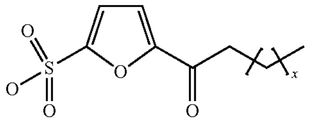

where X is 6 to 40

An additional example of an OFS surfactant includes:

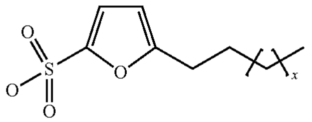

where X is 6 to 40.

An additional example of an OFS surfactant includes:

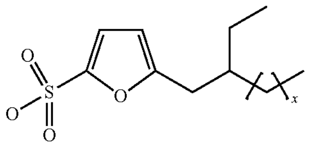

where X is 6 to 40.

An additional example of an OFS surfactant includes:

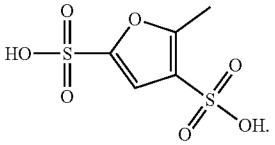

An additional example of an OFS surfactant includes:

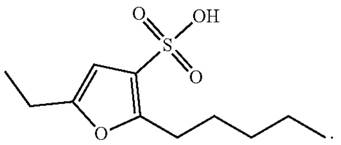 [SMILES: CCCCCc1oc(CC)cc1S(=O)(=O)O]

An additional example of an OFS surfactant includes:

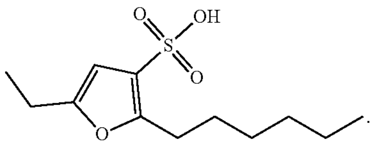 [SMILES: CCCCCCc1oc(CC)cc1S(=O)(=O)O]

An additional example of an OFS surfactant includes:

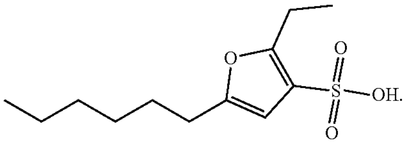 [SMILES: CCCCCCc1cc(S(=O)(=O)O)c(CC)o1]

An additional example of an OFS surfactant includes:

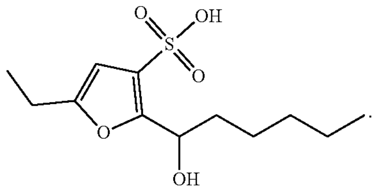 [SMILES: CCCCCC(O)c1oc(CC)cc1S(=O)(=O)O]

An additional example of an OFS surfactant includes:

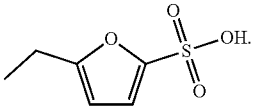

An additional example of an OFS surfactant includes:

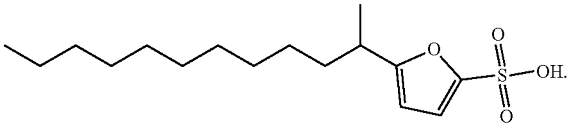 [SMILES: CCCCCCCCCCC(C)c1ccc(S(=O)(=O)O)o1]

An additional example of an OFS surfactant includes:

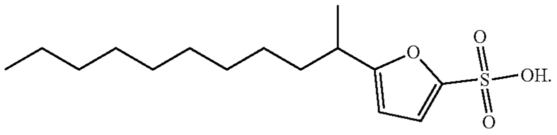 [SMILES: CCCCCCCCCC(C)c1ccc(S(=O)(=O)O)o1]

An additional example of an OFS surfactant includes:

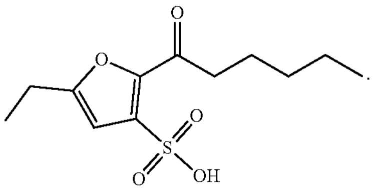 [SMILES: CCCCCC(=O)c1oc(CC)cc1S(=O)(=O)O]

An additional example of an OFS surfactant includes:

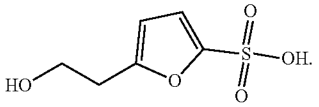 [SMILES: O=S(=O)(O)c1ccc(CCO)o1]

An additional example of an OFS surfactant includes:

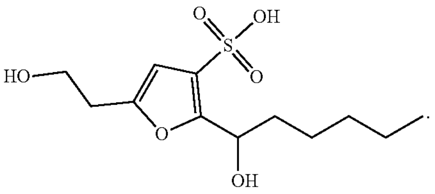 [SMILES: CCCCCC(O)c1oc(CCO)cc1S(=O)(=O)O]

The OFS surfactants may be of benefit in treatment fluid operations using hard brines as the base fluid or in treatment fluid operations in which the treatment fluid may contact a hard brine downhole. In treatment fluid operations in which the treatment fluid contacts a hard brine downhole, the hard brine may be introduced to or generated in the subterranean formation via another wellbore operation, or the hard brine may be a fluid native to the subterranean formation. The OFS surfactant may be of particular importance where the hard brine comprises a high concentration of cations, for example, in brines with a cation concentration of 10,000 ppm to 400,000 ppm or greater. General examples of the cations include any mono-, di-, or trivalent cation. Specific examples of the cations include, but are not limited to, ions of Na, K, Ca, Mg, Ba, Fe, or any combination thereof.

The concentration of the OFS surfactant in the treatment fluid may range from about 0.001% (w/w) to about 10% (w/w). The concentration may range from any lower limit to any upper limit and encompass any subset between the upper and lower limits. Some of the lower limits listed may be greater than some of the listed upper limits. One skilled in the art will recognize that the selected subset may require the selection of an upper limit in excess of the selected lower limit. Therefore, it is to be understood that every range of values is encompassed within the broader range of values. For example, the concentration of the OFS surfactant in the treatment fluid may range from about 0.001% (w/w) to about 10% (w/w), from about 0.005% (w/w) to about 10% (w/w), from about 0.01% (w/w) to about 10% (w/w), from about 0.05% (w/w) to about 10% (w/w), from about 0.1% (w/w) to about 10% (w/w), from about 0.5% (w/w) to about 10% (w/w), from about 1% (w/w) to about 10% (w/w), from about 2% (w/w) to about 10% (w/w), from about 3% (w/w) to about 10% (w/w), from about 4% (w/w) to about 10% (w/w), from about 5% (w/w) to about 10% (w/w), from about 6% (w/w) to about 10% (w/w), from about 7% (w/w) to about 10% (w/w), from about 8% (w/w) to about 10% (w/w), or from about 9% (w/w) to about 10% (w/w). As another example, the concentration of the OFS surfactant in the treatment fluid may range from about 0.001% (w/w) to about 10% (w/w), from about 0.001% (w/w) to about 9% (w/w), from about 0.001% (w/w) to about 8% (w/w), from about 0.001% (w/w) to about 7% (w/w), from about 0.001% (w/w) to about 6% (w/w), from about 0.001% (w/w) to about 5% (w/w), from about 0.001% (w/w) to about 4% (w/w), from about 0.001% (w/w) to about 3% (w/w), from about 0.001% (w/w) to about 2% (w/w), from about 0.001% (w/w) to about 1% (w/w), from about 0.001% (w/w) to about 0.5% (w/w), from about 0.001% (w/w) to about 0.1% (w/w), from about 0.001% (w/w) to about 0.05% (w/w), from about 0.001% (w/w) to about 0.01% (w/w), or from about 0.001% (w/w) to about 0.005% (w/w). With the benefit of this disclosure, one of ordinary skill in the art will be readily able to prepare a treatment fluid having a sufficient concentration of the OFS surfactant for a given application.

In fracturing or stimulating wellbore operations, the treatment fluid may comprise a polymer as the treatment fluid additive. The polymer may be a friction reducing polymer. The polymer may be susceptible to interaction with a cation, for example, a metal ion. This interaction may result in a conformation change in the polymer. In some examples, the polymer may form a polymer-metal complex with a metal cation. In some examples, the polymer may be anionic, cationic, or amphoteric. In some examples, the polymer is a partially hydrolyzed polymer. In some examples, the polymer is a polyacrylamide-based polymer. In some examples, the polymer does not comprise sulfonic and/or hydrophobic monomers. For example, the polymer may not be constructed from [2-(acryloyloxy)ethyl]trimethylammonium chloride monomers, 2-acrylamido-2-methylpropane sulfonic acid monomers, and/or any monomers which may functionalize the polymer to improve salt tolerance. The OFS surfactants form stable micelles or aggregations that may surround or solvate the polymer or other species of treatment fluid additive in the core of the micelle or internal portion of the aggregate. The polar head group of the micelles or aggregates interacts with the ions (e.g., cations) in the surrounding treatment fluid to form a structure that internalizes the nonpolar regions of the OFS surfactants. Within this internalized nonpolar region, the treatment fluid additive may be disposed, thereby solvating the treatment fluid additive within the micelles or aggregates formed by the OFS surfactants. This process improves the solubility of the treatment fluid additive in the treatment fluid and prevents interaction of the treatment fluid additive with cations present in the treatment fluid. As discussed above, the Stern layer of the formed micelle may be increased as the size of the polar head group of the OFS surfactant is increased relative to non-OFS surfactants. This increase in the Stern layer may result in the OFS surfactants repelling the cations further from the treatment fluid additive solvated in the micelle core relative to a non-OFS surfactant having a smaller polar head group.

The concentration of the polymer in the treatment fluid may range from about 0.001% (w/w) to about 20% (w/w). The concentration may range from any lower limit to any upper limit and encompass any subset between the upper and lower limits. Some of the lower limits listed may be greater than some of the listed upper limits. One skilled in the art will recognize that the selected subset may require the selection of an upper limit in excess of the selected lower limit. Therefore, it is to be understood that every range of values is encompassed within the broader range of values. For example, the concentration of the polymer in the treatment fluid may range from about 0.001% (w/w) to about 20% (w/w), from about 0.005% (w/w) to about 20% (w/w), from about 0.01% (w/w) to about 20% (w/w), from about 0.05% (w/w) to about 20% (w/w), from about 0.1% (w/w) to about 20% (w/w), from about 0.5% (w/w) to about 20% (w/w), from about 1% (w/w) to about 20% (w/w), from about 3% (w/w) to about 20% (w/w), from about 5% (w/w) to about 20% (w/w), from about 10% (w/w) to about 20% (w/w), or from about 15% (w/w) to about 20% (w/w). As another example, the concentration of the polymer in the treatment fluid may range from about 0.001% (w/w) to about 20% (w/w), from about 0.001% (w/w) to about 15% (w/w), from about 0.001% (w/w) to about 10% (w/w), from about 0.001% (w/w) to about 5% (w/w), from about 0.001% (w/w) to about 3% (w/w), from about 0.001% (w/w) to about 1% (w/w), from about 0.001% (w/w) to about 0.5% (w/w), from about 0.001% (w/w) to about 0.1% (w/w), from about 0.001% (w/w) to about 0.05% (w/w), from about 0.001% (w/w) to about 0.01% (w/w), or from about 0.001% (w/w) to about 0.005% (w/w). With the benefit of this disclosure, one of ordinary skill in the art will be readily able to prepare a treatment fluid having a sufficient concentration of the polymer for a given application.

The treatment fluids described herein comprise an aqueous fluid, for example, freshwater, saltwater (e.g., water containing one or more salts dissolved therein), brine (e.g., saturated saltwater, including saturated saltwater produced from subterranean formations), seawater, or any combination thereof. In the case of brines, the aqueous fluid may comprise a monovalent brine, a divalent brine, or a trivalent brine. Suitable monovalent brines may include, for example, sodium chloride brines, sodium bromide brines, potassium chloride brines, potassium bromide brines, and the like. Suitable divalent brines can include, for example, magnesium chloride brines, calcium chloride brines, calcium bromide brines, and the like. As discussed above, the OFS surfactants may be of particular importance in hard brines (e.g., saturated saltwater, including saturated saltwater produced from subterranean formations) having high salinity. In examples utilizing a hard brine, the concentration of the total cations in the aqueous fluid may exceed 10,000 ppm. In some examples, the concentration of the total cations in the brine may be between 10,000 ppm and 400,000 ppm. For example, the aqueous fluid used as the base fluid for the treatment fluid may comprise a Ca' concentration of greater than 10,000 ppm. One of ordinary skill in the art, with the benefit of this disclosure, should be readily able to select an aqueous fluid for a chosen application.

In some examples, the treatment fluid may not comprise salt-tolerant additives. These additives may any additive used to increase the salt-tolerance of the other treatment fluid additives in the treatment fluid. Generally, the salt-tolerant additives may function by reducing the potential interaction of a treatment fluid additive with a cation, for example, through sequestration of the cation. Examples of salt-tolerant additives include, but are not limited to, chelants such as ethylenediaminetetraacetic acid, ethylenediamine, phosphates, zeolites, citrates, polycarboxylates, sodium tripolyphosphates, or any combination thereof. Other examples of salt-tolerant additives include cationic surfactants, dimeric ammonium salts, and the like. One of ordinary skill in the art, with the benefit of this disclosure, will be readily able to identify a salt-tolerant additive and to prepare a treatment fluid without said salt-tolerant additive for a chosen application.

The treatment fluid may be any fluid in which it is desirable to prevent interaction of a treatment fluid additive with a cation. For example, the treatment fluid may be a fluid in which a polymeric material, or more specifically, a partially hydrolyzed, anionic polymer may undergo an undesired conformation change if it interacts with a cation. As another example, the treatment fluid may be a fluid in which certain nanoparticles, such as nano-sized silicon dioxide are used. These materials may be susceptible to salt-screening from elevated levels of multivalent cations. The OFS surfactant may improve the efficacy of these nanoparticle treatment fluids. As another example, the treatment fluid may be a fluid comprising a microemulsion susceptible to breaking in high salinity fluids. Examples of treatment fluids include, but are not limited to, fracturing fluids, acidizing fluids, polymer flooding fluids for enhanced oil recovery, production fluids, cements, drilling fluids, and fluids for coiled tubing milling.

In some optional examples, the treatment fluid may further comprise a pH adjustor. The pH adjustor may be any chemical agent sufficient for adjusting the pH of the treatment fluid to a desired range without negatively impacting the functionality of the other treatment fluid components. In some examples, the pH range of the treatment fluid is about 2 to about 12. General examples of the pH adjustor include, but are not limited to, hydroxides, borates, formates, acetates, carbonates, carbamates, phosphates, phosphonates, sulfates, sulfonates, or any combinations thereof. A preferred example of the pH adjustor is ammonium hydroxide. In some examples, a high pH range may be preferred such as if the fluid is a brine. In some examples, the pH range may be adjusted to be greater than 7.

In some optional examples, the treatment fluid may contain a pH control agent (e.g., a buffer) such as carbonate or bicarbonate to prevent rapid changes in pH. In some examples, the treatment fluid does not comprise a pH control agent. Examples of pH control agents include, but are not limited to, hydroxide, carbonates, amines, phosphates, dihydrogen phosphate, monohydrogen phosphate, sulfates and bisulfates, sulfites and bisulfite, formic acid, acetic acid.

In some optional examples, the treatment fluid may comprise an additive. The additive may be used to adjust a property of the treatment fluid, for example, viscosity, density, etc. Examples of the additives include, but are not limited to, corrosion inhibitors, surfactants, gel stabilizers, anti-oxidants, polymer degradation prevention additives, relative permeability modifiers, scale inhibitors, foaming agents, defoaming agents, antifoaming agents, iron control agents, particulate diverters, salts, fluid loss control additives, gas, catalysts, clay control agents, dispersants, flocculants, scavengers (e.g., $H_2S$ scavengers, $CO_2$ scavengers or $O_2$ scavengers), gelling agents, lubricants, friction reducers, bridging agents, viscosifiers, weighting agents, solubilizers, paraffin/asphaltenes inhibitors, emulsion breaker, hydrate inhibitors, consolidating agents, bactericides, clay stabilizers, breakers, delayed release breakers, the like, or any combination thereof. With the benefit of this disclosure, one of ordinary skill in the art will be able to formulate a treatment fluid having properties suitable for a desired application.

The present disclosure provides treatment fluids, methods, and systems for treating a subterranean formation. The treatment fluids include an OFS surfactant, a polymeric friction reducer and/or polymeric drag reducer, and a brine. The methods may include preparing a treatment fluid comprising the OFS surfactant. The methods may include pumping the treatment fluid in a wellbore penetrating a subterranean formation. The methods may also include introducing the treatment fluid into a portion of the subterranean formation from the wellbore. The systems may include pumping and mixing equipment to convey the treatment fluid to the interval of the wellbore comprising the target subterranean formation.

Example systems may comprise a pump fluidly coupled to a tubular, the tubular containing a treatment fluid as described herein. The pump may be a high-pressure pump. As used herein, the term “high-pressure pump” will refer to a pump that is capable of delivering a fluid downhole at a pressure of about 1000 psi or greater. A high-pressure pump may be used when it is desired to introduce the treatment fluid to a subterranean formation at or above a fracture gradient of the subterranean formation, but it may also be used in cases where fracturing is not desired. In some examples, the high-pressure pump may be capable of fluidly conveying particulate matter, such as proppant particulates, into the subterranean formation. Suitable high-pressure pumps will be known to one having ordinary skill in the art and may include, but are not limited to, floating piston pumps and positive displacement pumps. In other examples, the pump may be a low-pressure pump. As used herein, the term "low-pressure pump" will refer to a pump that operates at a pressure less than about 1000 psi. In some examples, a low-pressure pump may be fluidly coupled to a high-pressure pump that is fluidly coupled to the tubular. That is, the low-pressure pump may be configured to convey the treatment fluid to the high-pressure pump. In such examples, the low-pressure pump may "step up" the pressure of the treatment fluid before it reaches the high-pressure pump. In any example, a high-pressure pump and/or a low-pressure pump may convey the treatment fluid to the location of a target subterranean formation. The pumps may supply sufficient pressure to allow the treatment fluid to fracture the subterranean formation. That is, the pumps may meet or exceed the fracture gradient of the subterranean formation.

In some examples, the systems described herein may further comprise a mixing tank that is upstream of the pump and is the vessel in which the treatment fluid is formulated. In various examples, the pump (e.g., a low-pressure pump, a high-pressure pump, or a combination thereof) may convey the treatment fluid from the mixing tank to the transporting conduit. In other examples, the treatment fluid may be formulated offsite and transported to a worksite, in which case the treatment fluid may be introduced to the transporting conduit via the pump either directly from its shipping container (e.g., a truck, a railcar, a barge, or the like) or from a transport pipeline. In either case, the treatment fluid may be drawn into the pump, elevated to an appropriate pressure, and then introduced into the transporting conduit for delivery downhole.

When desired for use, the OFS surfactant may be added to aqueous fluid and the polymer and mixed as desired. In alternative examples, the OFS surfactant may be added to the aqueous fluid followed by a polymer or other treatment fluid additive(s) and then mixed as desired. In some examples, the polymer may be hydrated before it is introduced to the aqueous fluid. The components and additives of the treatment fluid may be added or introduced to one another in any order and at any time during the use of the treatment fluid.

FIG. 1 illustrates a schematic of the surface and near-surface portions of a system that can deliver the treatment fluids described herein to a downhole location, according to one or more examples. It should be noted that while FIG. 1 generally depicts a land-based system, it is to be recognized that like systems may be operated in subsea locations as well. As depicted in FIG. 1, system 100 may include mixing tank 105, in which a treatment fluid comprising an OFS surfactant and a polymer susceptible to interaction with a cation may be formulated. In some examples, the polymer may be a friction reducer. In more particular examples, the polymer is a partially hydrolyzed polyacrylamide. The treatment fluid may be conveyed via line 110 to wellhead 115, where the treatment fluid enters tubular 120. Tubular 120 may extend from wellhead 115 into a wellbore 125 penetrating subterranean formation 130. Wellbore 125 may be any type of wellbore including vertical, horizontal, deviated, etc. The illustrated portion of wellbore 125 is cased with a casing 135. It is to be understood that in some examples wellbore 125 may be uncased. Upon being ejected from tubular 120, the treatment fluid may subsequently enter into subterranean formation 130 as described in FIG. 2 below. Pump 140 may be configured to raise the pressure of the treatment fluid to a desired degree before its introduction into tubular 120. Examples of treatment fluids may include, but are not limited to, fracturing fluids, acidizing fluids, fluids used for enhanced oil recovery, production fluids, cements, drilling fluids, or any such fluids comprising treatment fluid additives which may undesirably interact with cations present in the treatment fluid or the subterranean formation 130.

Although not depicted in FIG. 1, the treatment fluid may, in some examples, flow back to wellhead 115 and exit subterranean formation 130. In some optional examples, the treatment fluid that has flowed back to wellhead 115 may subsequently be recovered and recirculated to subterranean formation 130. As the treatment fluid comprises the OFS surfactant, the treatment fluid additives (e.g., a friction reducing polymer) may not interact with the cations present in the treatment fluid and/or the subterranean formation 130. As such, the treatment fluid additives may be in a substantially similar state upon recovery to that of their introduction.

Figure 2:
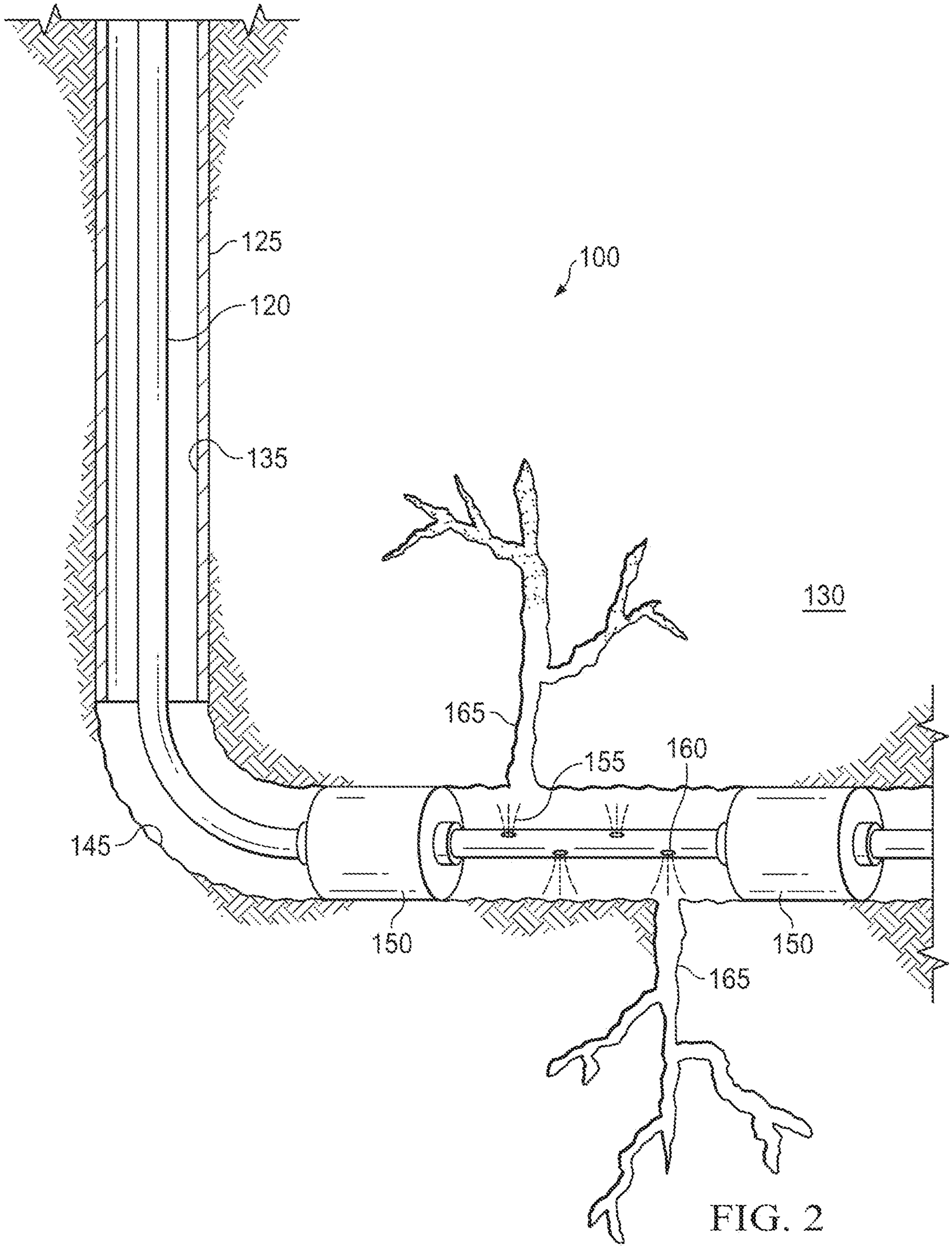
FIG. 2 is a schematic illustrating the placement of a treatment fluid into a fracture in a subterranean formation in accordance with one or more examples described herein.

FIG. 2 illustrates a schematic of the downhole portion of the system 100 illustrated in FIG. 1, according to one or more examples. As depicted in FIG. 2, tubular 120 extends from the wellhead 115 (as illustrated in FIG. 1) into wellbore 125 penetrating subterranean formation 130. After descending through the heel 145 of the wellbore 125, tubular 120 may be coupled to one or more packers 150 positioned to isolate an interval of wellbore 125. A treatment fluid 155, as described herein, may exit tubular 120 through openings 160. The treatment fluid 155 may be introduced into the subterranean formation 130 via a primary fracture 165 of other such opening into the subterranean formation 130. If the treatment fluid 155 is a fracturing fluid, it may have created or enhanced the primary fracture 165. If the treatment fluid 155 is an acidizing fluid, it may contact the walls of the subterranean formation 130, and also the channels within the primary fracture 165 and increase hydrocarbon permeability therethrough. If the treatment fluid 155 is an enhanced oil recovery fluid, it may be partially miscible with, or otherwise assist in conveying, a hydrocarbon fluid flowing out of the subterranean formation 130, thus enhancing hydrocarbon recovery from the subterranean formation 130.

It is to be recognized that system 100 is merely exemplary in nature, and various additional components may be present that have not necessarily been depicted in FIGS. 1 and 2 in the interest of clarity. Non-limiting additional components that may be present include, but are not limited to, supply hoppers, valves, condensers, adapters, joints, gauges, sensors, compressors, pressure controllers, pressure sensors, flow rate controllers, flow rate sensors, temperature sensors, and the like.

It should be clearly understood that the examples illustrated by FIGS. 1 and 2 are merely general applications of the principles of this disclosure in practice, and a wide variety of other examples are possible. Therefore, the scope of this disclosure is not limited in any manner to the details of FIGS. 1 and 2 as described herein.

It is also to be recognized that the disclosed treatment fluids may also directly or indirectly affect the various downhole equipment and tools that may contact the treatment fluids disclosed herein. Such equipment and tools may include, but are not limited to, wellbore casing, wellbore liner, completion string, insert strings, drill string, coiled tubing, slickline, wireline, drill pipe, drill collars, mud motors, downhole motors and/or pumps, surface-mounted motors and/or pumps, centralizers, turbolizers, scratchers, floats (e.g., shoes, collars, valves, etc.), logging tools and related telemetry equipment, actuators (e.g., electromechanical devices, hydromechanical devices, etc.), sliding sleeves, production sleeves, plugs, screens, filters, flow control devices (e.g., inflow control devices, autonomous inflow control devices, outflow control devices, etc.), couplings (e.g., electro-hydraulic wet connect, dry connect, inductive coupler, etc.), control lines (e.g., electrical, fiber optic, hydraulic, etc.), surveillance lines, drill bits and reamers, sensors or distributed sensors, downhole heat exchangers, valves and corresponding actuation devices, tool seals, packers, cement plugs, bridge plugs, and other wellbore isolation devices, or components, and the like. Any of these components may be included in the methods and systems generally described above and depicted in FIGS. 1-2.

Provided are methods of treating a subterranean formation in accordance with the disclosure. An example method comprises introducing a treatment fluid into a wellbore penetrating the subterranean formation, the treatment fluid comprising: an oleofuransulfonate surfactant; a treatment fluid additive capable of interaction with a cation; and an aqueous fluid. The cation is present in the treatment fluid or contacts the treatment fluid. The method further comprises solvating the treatment fluid additive with the oleofuransulfonate surfactant.

Additionally or alternatively, the method may include one or more of the following features individually or in combination. The oleofuransulfonate surfactant may be selected from the group consisting of 5-(1-oxododecyl)-2-furansulfonic acid; 5-(1-hexatetradecyl)-2-furansulfonic acid; 5-(1-oxohexadecyl)-2-furansulfonic acid; 5-(1-oxooctadecyl)-2-furansulfonic acid; 5-heptyl-2-furansulfonic acid; 5-dodecyl-2-furansulfonic acid; 5-tridecyl-2-furansulfonic acid; 5-tetradecyl-2-furansulfonic acid; 5-octadecyl-2-furansulfonic acid; 5-(2-ethyldodecyl)-2-furansulfonic acid; 5-methyl-2,4-furandisulfonic acid; 5-ethyl-2-pentyl-3-furansulfonic acid; 5-ethyl-2-hexyl-3-furansulfonic acid; 2-ethyl-5-hexyl-3-furansulfonic acid; 5-ethyl-2-(1-hydroxyhexyl)-3-furansulfonic acid; 5-ethyl-2-furansulfonic acid; 5-(1-methylundecyl)-2-furansulfonic acid; 5-(1-methyldecyl)-2-furansulfonic acid; 5-ethyl-2-(1-hydroxyhexyl)-3-furansulfonic acid; 5-ethyl-2-(1-oxohexyl)-3-furansulfonic acid; 5-(2-hydroxyethyl)-2-furansulfonic acid; 5-(2-hydroxyethyl)-2-(1-hydroxyhexyl)-3-furansulfonic acid; any salts thereof; any derivatives thereof; and any combination thereof. The treatment fluid may be a fracturing fluid, acidizing fluid, polymer flooding fluid for enhanced oil recovery, cement, drilling fluid, production fluid, or a fluid for coiled tubing milling. The treatment fluid additive may be a friction reducing polymer. The friction reducing polymer may be a polyacrylamide. The treatment fluid additive may be a polymer, and the polymer may not comprise a sulfonate-based and/or cationic monomer. The treatment fluid additive may be a polymer and the polymer may not be constructed from [2-(acryloyloxy)ethyl]trimethylammonium chloride monomers and/or 2-acrylamido-2-methylpropane sulfonic acid monomers. The treatment fluid additive may be nano-sized silicon dioxide. The treatment fluid may not comprise a chelant, a cationic surfactant, or a dimeric ammonium salt. The treatment fluid may not comprise ethylenediaminetetraacetic acid, ethylenediamine, phosphates, zeolites, citrates, polycarboxylates, sodium tripolyphosphates, or any combination thereof. The concentration of the cation in the aqueous fluid may be 10,000 ppm or greater. The cation may be an ion of Na, K, Ca, Mg, Ba, Fe, or a combination thereof.

Provided are treatment fluid compositions in accordance with the disclosure. An example treatment fluid composition comprises an oleofuransulfonate surfactant; a treatment fluid additive capable of interaction with a cation; and an aqueous fluid.

Additionally or alternatively, the treatment fluid may include one or more of the following features individually or in combination. The oleofuransulfonate surfactant may be selected from the group consisting of 5-(1-oxododecyl)-2-furansulfonic acid; 5-(1-hexatetradecyl)-2-furansulfonic acid; 5-(1-oxohexadecyl)-2-furansulfonic acid; 5-(1-oxooctadecyl)-2-furansulfonic acid; 5-heptyl-2-furansulfonic acid; 5-dodecyl-2-furansulfonic acid; 5-tridecyl-2-furansulfonic acid; 5-tetradecyl-2-furansulfonic acid; 5-octadecyl-2-furansulfonic acid; 5-(2-ethyldodecyl)-2-furansulfonic acid; 5-methyl-2,4-furandisulfonic acid; 5-ethyl-2-pentyl-3-furansulfonic acid; 5-ethyl-2-hexyl-3-furansulfonic acid; 2-ethyl-5-hexyl-3-furansulfonic acid; 5-ethyl-2-(1-hydroxyhexyl)-3-furansulfonic acid; 5-ethyl-2-furansulfonic acid; 5-(1-methylundecyl)-2-furansulfonic acid; 5-(1-methyldecyl)-2-furansulfonic acid; 5-ethyl-2-(1-hydroxyhexyl)-3-furansulfonic acid; 5-ethyl-2-(1-oxohexyl)-3-furansulfonic acid; 5-(2-hydroxyethyl)-2-furansulfonic acid; 5-(2-hydroxyethyl)-2-(1-hydroxyhexyl)-3-furansulfonic acid; any salts thereof; any derivatives thereof and any combination thereof. The treatment fluid may be a fracturing fluid, acidizing fluid, polymer flooding fluid for enhanced oil recovery, cement, drilling fluid, production fluid, or a fluid for coiled tubing milling. The treatment fluid additive may be a friction reducing polymer. The friction reducing polymer may be a polyacrylamide. The treatment fluid additive may be a polymer, and the polymer may not comprise a sulfonate-based and/or cationic monomer. The treatment fluid additive may be a polymer and the polymer may not be constructed from [2-(acryloyloxy)ethyl]trimethylammonium chloride monomers and/or 2-acrylamido-2-methylpropane sulfonic acid monomers. The treatment fluid additive may be nano-sized silicon dioxide. The treatment fluid may not comprise a chelant, a cationic surfactant, or a dimeric ammonium salt. The treatment fluid may not comprise ethylenediaminetetraacetic acid, ethylenediamine, phosphates, zeolites, citrates, polycarboxylates, sodium tripolyphosphates, or any combination thereof. The concentration of the cation in the aqueous fluid may be 10,000 ppm or greater. The cation may be an ion of Na, K, Ca, Mg, Ba, Fe, or a combination thereof.

Provided are systems for treating a subterranean formation in accordance with the disclosure. An example system comprises a treatment fluid comprising: an oleofuransulfonate surfactant; a treatment fluid additive capable of interaction with a cation; and an aqueous fluid. The system further comprises mixing equipment configured to mix the oleofuransulfonate surfactant, the treatment fluid additive, and the aqueous fluid; and a pump fluidly coupled to a tubular extending into a wellbore penetrating the subterranean formation, wherein the tubular is configured to circulate or otherwise convey the treatment fluid in the wellbore.

Additionally or alternatively, the system may include one or more of the following features individually or in combination. The oleofuransulfonate surfactant may be selected from the group consisting of 5-(1-oxododecyl)-2-furansulfonic acid; 5-(1-hexatetradecyl)-2-furansulfonic acid; 5-(1- oxohexadecyl)-2-furansulfonic acid; 5-(1-oxooctadecyl)-2-furansulfonic acid; 5-heptyl-2-furansulfonic acid; 5-dodecyl-2-furansulfonic acid; 5-tridecyl-2-furansulfonic acid; 5-tetradecyl-2-furansulfonic acid; 5-octadecyl-2-furansulfonic acid; 5-(2-ethyldodecyl)-2-furansulfonic acid; 5-methyl-2,4-furandisulfonic acid; 5-ethyl-2-pentyl-3-furansulfonic acid; 5-ethyl-2-hexyl-3-furansulfonic acid; 2-ethyl-5-hexyl-3-furansulfonic acid; 5-ethyl-2-(1-hydroxyhexyl)-3-furansulfonic acid; 5-ethyl-2-furansulfonic acid; 5-(1-methylundecyl)-2-furansulfonic acid; 5-(1-methyldecyl)-2-furansulfonic acid; 5-ethyl-2-(1-hydroxyhexyl)-3-furansulfonic acid; 5-ethyl-2-(1-oxohexyl)-3-furansulfonic acid; 5-(2-hydroxyethyl)-2-furansulfonic acid; 5-(2-hydroxyethyl)-2-(1-hydroxyhexyl)-3-furansulfonic acid; any salts thereof; any derivatives thereof; and any combination thereof. The treatment fluid may be a fracturing fluid, acidizing fluid, polymer flooding fluid for enhanced oil recovery, cement, drilling fluid, production fluid, or a fluid for coiled tubing milling. The treatment fluid additive may be a friction reducing polymer. The friction reducing polymer may be a polyacrylamide. The treatment fluid additive may be a polymer, and the polymer may not comprise a sulfonate-based and/or cationic monomer. The treatment fluid additive may be a polymer and the polymer may not be constructed from [2-(acryloyloxy)ethyl]trimethylammonium chloride monomers and/or 2-acrylamido-2-methylpropane sulfonic acid monomers. The treatment fluid additive may be nano-sized silicon dioxide. The treatment fluid may not comprise a chelant, a cationic surfactant, or a dimeric ammonium salt. The treatment fluid may not comprise ethylenediaminetetraacetic acid, ethylenediamine, phosphates, zeolites, citrates, polycarboxylates, sodium tripolyphosphates, or any combination thereof. The concentration of the cation in the aqueous fluid may be 10,000 ppm or greater. The cation may be an ion of Na, K, Ca, Mg, Ba, Fe, or a combination thereof.

The preceding description provides various examples of the systems and methods of use disclosed herein which may contain different method steps and alternative combinations of components. It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps. The systems and methods can also "consist essentially of" or "consist of the various components and steps." Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as ranges from any lower limit may be combined with any other lower limit to recite a range not explicitly recited. In the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

One or more illustrative examples incorporating the examples disclosed herein are presented. Not all features of a physical implementation are described or shown in this application for the sake of clarity. Therefore, the disclosed systems and methods are well adapted to attain the ends and advantages mentioned, as well as those that are inherent therein. The particular examples disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown other than as described in the claims below. It is therefore evident that the particular illustrative examples disclosed above may be altered, combined, or modified, and all such variations are considered within the scope of the present disclosure. The systems and methods illustratively disclosed herein may suitably be practiced in the absence of any element that is not specifically disclosed herein and/or any optional element disclosed herein.

Although the present disclosure and its advantages have been described in detail, it should be understood that various changes, substitutions and alterations can be made herein without departing from the spirit and scope of the disclosure as defined by the following claims.

What is claimed is:

1. A method for treating a subterranean formation, the method comprising:

introducing a treatment fluid into a wellbore penetrating the subterranean formation, the treatment fluid comprising:

an oleofuransulfonate surfactant;

a treatment fluid additive; and an aqueous fluid;

wherein a cation is present in the treatment fluid or contacts the treatment fluid, and the treatment fluid additive is capable of interaction with the cation; and solvating the treatment fluid additive with the oleofuransulfonate surfactant.

2. The method of claim 1, wherein the oleofuransulfonate surfactant is selected from the group consisting of 5-(1-oxododecyl)-2-furansulfonic acid; 5-(1-hexatetradecyl)-2-furansulfonic acid; 5-(1-oxohexadecyl)-2-furansulfonic acid; 5-(1-oxooctadecyl)-2-furansulfonic acid; 5-heptyl-2-furansulfonic acid; 5-dodecyl-2-furansulfonic acid; 5-tridecyl-2-furansulfonic acid; 5-tetradecyl-2-furansulfonic acid; 5-octadecyl-2-furansulfonic acid; 5-(2-ethyldodecyl)-2-furansulfonic acid; 5-methyl-2,4-furandisulfonic acid; 5-ethyl-2-pentyl-3-furansulfonic acid; 5-ethyl-2-hexyl-3-furansulfonic acid; 2-ethyl-5-hexyl-3-furansulfonic acid; 5-ethyl-2-(1-hydroxyhexyl)-3-furansulfonic acid; 5-ethyl-2-furansulfonic acid; 5-(1-methylundecyl)-2-furansulfonic acid; 5-(1-methyldecyl)-2-furansulfonic acid; 5-ethyl-2-(1-hydroxyhexyl)-3-furansulfonic acid; 5-ethyl-2-(1-oxohexyl)-3-furansulfonic acid; 5-(2-hydroxyethyl)-2-furansulfonic acid; 5-(2-hydroxyethyl)-2-(1-hydroxyhexyl)-3-furansulfonic acid; any salts thereof; and any combination thereof.

3. The method of claim 1, wherein the treatment fluid is a fracturing fluid, acidizing fluid, polymer flooding fluid for enhanced oil recovery, cement, drilling fluid, production fluid, or a fluid for coiled tubing milling.

4. The method of claim 1, wherein the treatment fluid additive is a polyacrylamide-based co-, or terpolymer.

5. The method of claim 1, wherein the treatment fluid additive is a polymer; and wherein the polymer does not comprise a sulfonate-based and/or cationic monomer.

6. The method of claim 1, wherein the treatment fluid additive is an acrylamide co-polymer; and wherein the acrylamide co-polymer is not constructed from [2-(acryloyloxy)ethyl]trimethylammonium chloride monomers and/or 2-acrylamido-2-methylpropane sulfonic acid monomers.

7. The method of claim 1, wherein the treatment fluid additive is nano-sized silicon dioxide.

8. The method of claim 1, wherein the treatment fluid does not comprise a chelant, a cationic surfactant, a dimeric ammonium salt ethylenediaminetetraacetic acid, ethylenediamine, phosphates, zeolites, citrates, polycarboxylates, sodium tripolyphosphates, or any combination thereof.

9. The method of claim 1, wherein the concentration of the cation in the aqueous fluid is 10,000 ppm or greater.

* * * * *